United States Patent [19]

Kleinerman

[11] Patent Number: 5,332,316
[45] Date of Patent: * Jul. 26, 1994

[54] FIBER OPTIC SYSTEMS FOR SENSING TEMPERATURE AND OTHER PHYSICAL VARIABLES

[76] Inventor: Marcos Y. Kleinerman, 24 Jerome St., Southbridge, Mass. 01550

[*] Notice: The portion of the term of this patent subsequent to Nov. 24, 2004 has been disclaimed.

[21] Appl. No.: 10,585

[22] Filed: Jan. 28, 1993

Related U.S. Application Data

[60] Division of Ser. No. 812,050, Dec. 23, 1991, Pat. No. 5,222,810, which is a continuation-in-part of Ser. No. 516,532, Apr. 30, 1990, Pat. No. 5,090,818, which is a division of Ser. No. 711,062, Mar. 12, 1985, Pat. No. 5,004,913, which is a continuation-in-part of Ser. No. 608,932, May 14, 1984, Pat. No. 4,708,494, which is a continuation of Ser. No. 405,732, Aug. 6, 1982, abandoned.

[51] Int. Cl.$^5$ .................. G01K 11/20; G01K 13/00
[52] U.S. Cl. .................. 374/161; 374/142; 374/143; 374/120; 356/44; 250/227.18; 250/227.23; 250/458.1
[58] Field of Search ............... 374/161, 142, 143, 131, 374/159, 121, 137, 120; 356/44; 250/458.1, 227.23, 227.18

[56] References Cited

U.S. PATENT DOCUMENTS

| | | | |
|---|---|---|---|
| Re. 31,832 | 2/1985 | Samulski | 374/131 |
| 4,075,493 | 2/1978 | Wickersheim | 374/159 |
| 4,374,328 | 2/1983 | Tekippe et al. | 250/461.1 |
| 4,376,890 | 3/1983 | Engström et al. | 250/227.23 |
| 4,378,496 | 3/1983 | Brogårdh et al. | 250/227.23 |
| 4,409,476 | 10/1983 | Lögfren et al. | 374/161 |
| 4,437,772 | 3/1984 | Samulski | 374/131 |
| 4,455,741 | 6/1984 | Kolodner | 374/161 |
| 4,539,473 | 9/1985 | Brogårdh et al. | 374/161 |
| 4,550,256 | 10/1985 | Berkstresser et al. | 250/486.1 |
| 4,562,348 | 12/1985 | Brogårdh et al. | 250/227.21 |
| 4,569,570 | 2/1986 | Brogårdh et al. | 250/486.1 |
| 4,607,158 | 8/1986 | Ovren | 250/216 |
| 4,626,110 | 12/1986 | Wickersheim et al. | 374/161 |
| 4,648,094 | 3/1987 | McCollum et al. | 372/41 |
| 4,652,143 | 3/1987 | Wickersheim et al. | 374/161 |
| 4,708,494 | 11/1987 | Kleinerman | 374/131 |
| 4,729,668 | 3/1988 | Angel et al. | 374/161 |
| 4,752,141 | 6/1988 | Sun et al. | 374/161 |
| 4,768,886 | 9/1988 | Hirschfeld et al. | 374/161 |
| 4,776,827 | 10/1988 | Greaves | 374/161 |
| 4,806,757 | 2/1989 | Kano et al. | 250/327.2 |
| 4,859,079 | 8/1989 | Wickersheim et al. | 374/161 |
| 4,880,972 | 11/1989 | Brodgårdh et al. | 374/161 |

FOREIGN PATENT DOCUMENTS 0146522  6/1985  European Pat. Off. ............ 374/161

OTHER PUBLICATIONS

McCormack, J. S., "Remote Optical Measurement of Temperature Using Luminescent Materials", Elektronics Letters 17, pp. 630–631 (1981).

Fonger, W. H., and C. W. Struck, "Temperature dependences of $Cr^{+3}$ radiative and nonradiative transitions in ruby and emerald", *Physical Review B, 11* pp. 3251–3260 (1975).

(List continued on next page.)

*Primary Examiner*—Diego F. F. Gutierrez

[57] ABSTRACT

The invention is drawn to methods and devices for measuring temperature with a simple probe, a single interrogating light source and a single photodetector in a manner that the same probe can be used for simultaneously sensing another physical parameter, using the same interrogating light source and the same photodetector. The invention also allows the use of a single probe for measuring temperature in two independent physical modes, using a single interrogating light source and a single photodetector. In a preferred embodiment the probe includes a photoluminescent material having a luminescence decay time which decreases substantially with increasing temperature over a temperature range within which its luminescence quantum efficiency remains approximately constant or varies only minimally.

17 Claims, 6 Drawing Sheets

OTHER PUBLICATIONS

Page 127 of the book "Optical Fiber Telecommunications" edited by S. E. Miller and A. G. Chynoweth (Academic Press, 1979).

G. Kemeny and C. H. Haake, "Activator Center in Magnesium Fluorogermanate Phosphors". *J. Chem. Phys.* 33, pp. 783–789 (1960).

Grattan et al., "Fibre-optic temperature sensor with wide temperature range characteristics", IEE Proceedings, vol. 134, pp. 291–294 (1987).

Lengyel, B. A., "Lasers", 2nd edition, Wiley-Interscience, New York (1971), Chapter 4, pp. 105–132 (Sections 4.1 to 4.3).

Sholes, R. R. et al., "Fluorescent decay thermometer with biological applications," Rev. Sci. Instrum., vol. 51, No. 7 (Jul. 1980).

Wickersheim, K. A. et al., "Recent Advances in Optical Temperature Measurement," Industrial Research/Development (Dec. 1979).

FIBER OPTIC SYSTEMS FOR SENSING TEMPERATURE AND OTHER PHYSICAL VARIABLES

CROSS-REFERENCE TO RELATED APPLICATIONS

This application is a division of co-pending application Ser. No. 07/812,050 filed Dec. 23, 1991, now U.S. Pat. No. 5,222,810 which is a continuation-in-part of application Ser. No. 7/516,532 filed Apr. 30, 1990, now U.S. Pat. No. 5,090,818, which is a division of application Ser. No. 711,062 filed Mar. 12, 1985, now U.S. Pat. No. 5,004,913, which in turn is a continuation-in-part of application Ser. No. 608,932 filed May 14, 1984, now U.S. Pat. No. 4,708,494, which in turn is a continuation of application Ser. No. 405,732 filed Aug. 6, 1982, now abandoned. The teachings of said prior applications are incorporated herein by reference.

BACKGROUND OF THE INVENTION

A fiber optic sensing system is a system wherein interrogating light is directed to a probe by fiber optic means, and light from the probe, with a property indicative of the sensed variable, is directed to photodet means.

The present invention relates to methods and devices for the measurement of physical parameters using a class of optical probes which permit the measurement of temperature by at least two physically independent optical methods, or the measurement of temperature in addition to at least another physical parameter, using a single optical probe, a single interrogating light source and a single photodetector, in conjunction with fiber optic techniques for directing interrogating to the probe and for directing light from the probe to the photodetector.

The term "light" in this application refers broadly to optical radiation, whether or not visible to the human eye. Although in the past the use of the word was restricted to visible radiation, workers in the art of fiber optics and lasers have generally adopted the broader coverage. Thus, the term "light-emitting diode" (LED) applies to a semiconductor source of infrared radiation just as well as to a source of red or yellow light. The word "Laser", which stands for Light Amplification by Stimulated Emission of Radiation, is not restricted to visible-emitting devices. In fact, most LED's and lasers are emitters of non-visible optical radiation, mostly infrared. And the "Light" in the term "Lightwave Communications" applies more often than not to optical radiation of wavelengths of about 1.3 or 1.55 micrometers ($\mu$m), in the infrared region.

Like almost all inventions relating to fiber optic sensors, all patented fiber optic temperature sensors make use of previously known physical principles, properties of matter and/or optical devices. The temperature-dependent properties of matter used in fiber optic temperature sensors include (but are not limited to) temperature-dependent changes in optical birefringence, light absorption, luminescence properties, light scattering or light phase.

Long before there were any fiber optic temperature sensors, U.S. Pat. No. 2,551,650 to Urbach described the use of some photoluminescent materials for sensing temperature changes of objects on which coatings of said materials were applied.

In 1972, U.S. Pat. No. 3,639,765, described how films of some photoluminescent materials doped with trivalent terbium and europium ions ($Tb^{3+}$ and $Eu^{3+}$) could map temperature distributions on the surfaces these films were applied to. These materials required excitation with ultraviolet radiation in order to operate. The temperature at each point in the film could be determined from measuring the intensity of the green component of the luminescence (emitted by $Tb^{3+}$) which decreased with increasing temperature, or the intensity of the red component (emitted by $Eu^{3+}$), which increased with increasing temperature. The patent also disclosed that the decrease of the $Tb^{3+}$ luminescence intensity was accompanied by a corresponding decrease of the luminescence decay time. In 1977, U.S. Pat. No. 4,061,578 introduced the technique of "spectrally-selective luminescence ratio thermometry", whereby the temperature at a sensing point is determined from the ratio of the intensities of two spectral components of the luminescence of the material (also known as "phosphor"). The main application considered in these patents was the conversion of a thermal infrared image into a visible image. The technique of spectrally-selective luminescence ratio thermometry was used later for fiber optic thermometry by Wickersheim et al. in U.S. Pat. Nos. 4,075,493 and 4,448,547, using phosphors also doped with trivalent europium ions, including phosphors previously described by Struck et al. (Struck, C. W. and Fonger W. H. Journal of Luminescene 1,2 [1970] 456–469) and by Wickershelm et al. (Wickersheim, K. A. and Buchanan, R. A. Appl. Phys. Letters 17, pp. 184–187 [1970]). A new company, Luxtron Corporation, was formed to market fiber optic temperature sensors based on Wickersheim's patents. These sensors required ultraviolet excitation and complex optical instrumentation requiring a plurality of optical filters, a plurality of lenses and mirrors, and a plurality of photodetectors, as shown in the last figure in the article by K. Wickersheim et al. "Recent Advances in Optical Temperature Measurement", Industrial Research/Development (December 1979).

An alternate technique for fiber optic temperature sensing uses the measurement of the decay time of the thermally quenched luminescence of some phosphors previously known for decades, including alkaline earth sulfides excited by ultraviolet or blue light pulses, and is the subject of U.S. Pat. No. 4,223,226 to Quick et al. and 4,245,507 (re-issued as Re. 31,832 Feb. 12, 1985) and 4,437,772 to Samulski. In addition to requiring ultraviolet or blue excitation light, which restricts the use of the technique to relatively short fiber distances, the light pulses required expensive light sources, and the luminescence efficiency of these phosphors decreased with increasing temperature over the temperature range of operation of the sensor, which restricted their use to relatively narrow temperature ranges. For example, FIG. 4 of U.S. Pat. No. Re. 31,832 shows that the luminescence efficiency of these phosphors decreases to one half of its initial value over a temperature range of only 29.9 kelvins.

Another example of a fiber optic temperature sensor based on the temperature-dependent decay time of thermally quenched luminescence was described by J. S. McCormack Electronics Letters 17, pp. 630–631 (1981). It requires ultraviolet or blue light excitation, so it is only a marginal improvement over the Samulski sensors.

Yet another temperature sensor based on thermally quenched luminescence uses the temperature-dependent luminescence decay time of the so-called "R" bands of ruby, as described in the Sholes and Small reference on record in the file of pending application Ser. No. 812,050.

An improvement of the technique of spectrally-selective luminescence ratio thermometry is described in U.S. Pat. No. 4,376,890 to Engström et al., who used a a probe a fluorescent semiconductor, and an GaAlAs LED as excitation source. But the device still had the disadvantage of requiring a relatively complex electro-optical system including (but not limited to) a plurality of optical filters and a plurality of photodetectors.

At the time of filing (Aug. 6, 1982) of applicant's original application for this invention (Ser. No. 405,732now abandoned) the only known fiber optic temperature sensors using luminescent probes required a temperature-dependent change in either the luminescence spectra of the probe or its luminescence quantum efficiency, or both. The only commercially available sensors were the ones based on the above Wickersheim patents requiring ultraviolet excitation, thermally quenched phosphors, and complex optical instrumentation requiring a plurality of optical filters, a plurality of lenses and a plurality of photodetectors, as shown in the article by K. Wickershelm et al., Industrial Research-/Development, December 1979 .

Kleinerman's patent application Ser. No. 405,732 filed Aug. 6, 1982, now abandoned, disclosed for the first time fiber optic temperature sensing systems using photoluminescent probes which did not require any temperature-dependent changes of any luminescence property for accurate temperature sensing, could be implemented with simple devices employing inexpensive and long-lived red or infrared LEDs, required no optical filters, lenses, mirrors or polarization-selective components, and could use as probes virtually any efficient photoluminescent material. Furthermore, the invention teaches that this technology can be applied to a special class of photoluminescent materials described in the section entitled "Luminescent materials with two emissive levels in thermal equilibrium" (U.S. Pat. No. 4,708,494, col. 13, line 19 to col. 14 line 53) and characterized by a luminescence decay time which decreases with increasing temperature over a wide temperature range within which the luminescence quantum efficiency is essentially constant, and that a temperature sensor based on said materials can be operated in two physically independent modes, thus allowing self-checking operation. This special kind of photoluminescent materials includes inorganic crystals doped with $3d^3$ transition metal ions comprising $Cr^{3+}$, $V^{2+}$ and $Mn^{4+}$. $Cr^{3+}$-doped materials like emerald, specifically discussed in U.S. Pat. No. 4,708,494, are known to be extremely stable to high excitation powers and high thermal stress. The luminescence physics of emerald have been described by W. H. Fonger and C. W. Struck, Physical Review B, 11 pp 3251-3260 (1975), as already discussed in said U.S. Pat. No. 4,708,494 (col. 16 lines 17-63). Nothing in the paper by Fonger and Struck suggests any use for fiber optic sensors or any other application.

According to the teachings of this invention such materials, characterized by an essentially constant luminescence quantum efficiency over a wide temperature range over which their luminescence time rate of decay varies substantially, can be used as temperature probes in a plurality of methods for the optical measurement of temperature. A single probe comprised of a single such material can be interrogated in one or a plurality of physically independent methods within a single simple device using a single inexpensive and very long-lived interrogating light source, preferably a light-emitting diode (LED), a single photodetector, and without requiring the use of optical filters. Because they can be interrogated in at least two physically independent methods, these materials can be used for constructing self-checking fiber optic temperature sensors using a single probe, a single interrogating light source and a single photodetector, as claimed in claims 7 and 18 of U.S. Pat. No. 4,708,494, claims 3 and 9 of U.S. Pat. No. 5,090,818 and in this application. They can also be used to construct hi-parametric sensors, namely sensors which can measure temperature and another independent physical parameter, again using a single probe, a single interrogating light source and a single photodetector. Their actual or proposed use according to the teachings of this invention was not reported, proposed, or even hinted at, to applicant's knowledge, before applicant's filing of the parent application Ser. No. 405,732, now abandoned. At that time, the only kinds of fiber optic temperature sensors based on probe luminescence commercially available or otherwise known in the open literature required were those discussed in the section entitled "Background of the invention" of the parent application Ser. No. 405,732 filed Aug. 6, 1982, now abandoned and its continuation application Ser. No. 668,932 filed May 14, 1984,now U.S. Pat. No. 4,708,494. All of these devices required ultraviolet or blue interrogating lights. The two main features in the new temperature sensors subject of these applications are:

(a) an optical signal from a probe generated at wavelengths $\lambda_1$ different from the wavelength or wavelengths of the interrogating light, and with an intensity which increases with increasing temperature over the temperature range of operation of the sensor; and/or (b) a luminescence from the same probe as in (a), with a decay time $\tau$ which varies substantially over a temperature range (several hundred kelvins for emerald) within which the luminescenes quantum efficiency remains constant or varies only minimally.

Sensors having the above features can be implemented (as described in U.S. Pat. No. 4,708,494) with inexpensive red or near infrared LED excitation sources.

The first publicly disclosed temperature sensor using feature (a) above was the distributed temperature sensor based on the previously known phenomenon of anti-Stokes Raman scattering, and was first disclosed in a British patent application filed on 1983 by J. P. Dakin, UK Patent Application GB 2 140 554 A, filed 26 May 1983. The term "anti-Stokes" means (to oversimplify) that the wavelengths $\lambda_1$ of the emitted light are shorter- than the wavelength or wavelengths of the interrogating light, as the part of the emitted light discussed and illustrated in Kleinerman's 1987 U.S. Pat. No. 4,708,494, col. 7, lines 4-28, and FIG. 2 (arrowed lines 70-71). Raman scattering from optical fibers, both Stokes and anti-Stokes, had been known in the art. Page 127 of the book "Optical Fiber Telecommunications" edited by S. E. Miller and A. G. Chynoweth (Academic Press, 1979), FIG. 5.1, shows both the Stokes and anti-Stokes bands of the Raman-scattered light of fused silica.

The first public disclosure of a fiber optic temperature sensor having feature (b) was made on September 1984 by (Bosselmann, A. Reule and J. Schróder, "Fiber-optic temperature sensor using fluorescence decay time", Proc. 2d Int. Conf. on Opt. Fiber Sensors, Stuttgart, FRG, pp. 151-154, September 1984, more than two years after the date of filing of Kleinerman's 1982 parent application Ser. No. 405,732, now abandoned. In 1985 the Luxtron Corporation began marketing a fiber optic sensor (U.S. Pat. No. 4,652,143) based on a probe comprised of $Mn^{4+}$-doped magnesium fluorogermanate, a phosphor with luminescence properties previously described by G. Kemeny and C. H. Haake, J. Chem. Phys. 33, pp. 783-789 (1960). This probe, with a luminescenes decay time $\tau$ which varies over a temperature range within which the luminescenes quantum efficiency remains constant or varies only minimally, was operated according to the teachings of Kleinerman's U.S. Pat. No. 4,708,494, section entitled "Luminescent materials with two emissive levels in thermal equilibrium", col. 13, line 19 to col. 14 line 53. However, the phosphor has the disadvantage that it requires ultraviolet or violet excitation light from a Xenon flashtube (see K. A. Wickersheim and M. H. Sun, J. Microwave Power, pp. 85-94 [1987]), a high voltage source which is inefficient, expensive and relatively short-lived. A further disadvantage of the $Mn^{4+}$-based Luxtron sensors is that their temperature coefficient of luminescence decay time is lower than 1 percent per °C., too low to be accurate for many applications.

The first commercially available fiber optic temperature sensor using as a probe a photoluminescent material with a temperature-dependent luminescence decay time an excitable with red or near infrared LEDs was announced by Wickersheim in 1991 in "Application of fiber optic thermometry to the monitoring of winding temperatures in medium and large power transformers", SPIE Proceedings Vol. 1584 [1991].

OBJECTIVES OF THE INVENTION

It is an objective of the present invention to provide fiber optic temperature measuring system using optical probes wherein a temperature-dependent fraction of the intensity of the interrogating light of pre-selected wavelengths is converted into a light emitted by the probe at wavelengths different and separable from those of the interrogating light, the intensity of said emitted light being an indicator of the probe temperature.

It is another objective of the present invention to provide fiber optic temperature measuring systems using probes characterized by easily measurable luminescence decay times which vary as a sensitive function of temperature, but without the disadvantage of significant luminescence quenching.

Another objective of the present invention is to provide fiber optic methods and devices using a single probe for measuring temperature in addition to another physical parameter like force or displacement, or for measuring temperature by two physically independent methods.

Yet another objective of this invention is to permit all the above methods, devices and systems to be operated in the red and/or near infrared spectral regions.

Other objectives of the present invention will become apparent from the description provided in the following sections of the specification.

The invention accordingly comprises the methods, materials, apparatuses and systems, together with their steps, parts, elements and interrelationships that are exemplified in the following disclosure, the scope of which will be indicated in the appended claims.

SUMMARY OF THE INVENTION

The objectives of this invention are accomplished by the use of fiber optic methods and devices for sensing physical parameters, said methods and devices using probes which can convert a parameter-dependent fraction $\alpha P_o$ of the intensity $P_o$ of the interrogating light of pre-selected wavelengths incident on the probe into a light emitted by the probe at wavelengths $\lambda_1$ different and separable from those of the interrogating light, the intensity of said emitted light being an indicator of the value (magnitude) of physical parameter acting on the probe. Preferred embodiments adapted to measure temperature use light-transmitting probes which cause the value of $\alpha$ to increase with increasing temperature. In such case the ratio of the intensity of the emitted light of wavelengths $\lambda_1$ to that of the transmitted interrogating light increases with increasing temperature, and this ratio can be used as a temperature indicator. The ratio is unaffected or minimally affected by fluctuations of the intensity of the interrogating light or by fiber and/or connector losses.

The light of wavelengths $\lambda_1$ emitted by some preferred probes includes wavelengths shorter than the wavelength or wavelengths of the interrogating light.

One preferred class of probes for temperature measurement is comprised of photoluminescent materials used in a new way. Before the Aug. 6, 1982 date of filing of the U.S. parent application Ser. No. 06/405,732, now abandoned, it was generally thought that the measurement of temperature with photoluminescent probes required a temperature-dependent change in the quantum efficiency, decay time or spectral distribution of the luminescence of the probe material. Only a relatively small number of photoluminescent materials could thus be used as temperature probes, most of them over a relatively small temperature range. Using physical principles previously known to molecular spectroscopists, this invention transforms the art radically by allowing the use of virtually all solid or liquid photoluminescent materials as temperature probes, without requiring any temperature-dependent change of any luminescence property of the probe material. The probes are used for the measurement of the absorption of interrogating light of a wavelength at which the light absorption is temperature-dependent. The luminescence of the probes permits the direct measurement of the fraction $\alpha P_o$ of the intensity $P_o$ of the interrogating light which is absorbed (and which is the temperature indicator), as opposed to the conventional, indirect estimate of $\alpha$ by ordinary light transmission measurements. Such indirect estimate of $\alpha$ was used in the prior art for fiber optic temperature measurement, as described in the U.S. Pat. No. 4,302,970 to Snitzer et al. The Snitzer patent (representative of other optical methods of temperature measurement based on temperature-dependent light absorption) describes the measurement of temperature by measuring the temperature-dependent light transmission of an optical fiber probe doped with rare earth ions. The superiority of luminescence conversion of the absorbed light according to this invention can be understood from the following example:

Suppose that one is measuring temperature by interrogating a light-transmissive probe having a temperature-dependent light absorption at a suitable wavelength. At some temperature $T_o$ the interrogating light entering the probe with an intensity $P_o$ is attenuated by a fraction $\alpha P_o$ of one percent of its original intensity, that is to an intensity of $P_o(1-\alpha)$, or $0.9900P_o$, the value of $\alpha$ being equal to 0.01. It is necessary to measure the temperature to an accuracy of one percent. Suppose that a temperature increase of 1° C. increases the value of $\alpha$ by one percent, to 0.0101, and decrease the intensity of the transmitted light to $0.9899P_o$. With prior art techniques one would have to estimate the change in the value of $\alpha$ indirectly, by measuring first the intensity of the light transmitted by the probe, that is $0.9900P_o$, and then $0.9899P_o$. This is a difference of one part in 10,000, which is not readily measurable with most industrial gages. And even if industrial gages could measure this difference accurately, the measurement would not be valid unless the intensity of the interrogating light itself could be held constant to better than one part in 10,000, which is difficult. If, for example, the stability of the light source were as good as one part per thousand, the temperature measurement would have an unacceptably high error of 10 percent, even with a perfect gage.

If, however, the otherwise lost fraction of the intensity of the interrogating light (that is, $\alpha P_o$) is converted into light emitted from the probe at wavelengths different from those of the interrogating light, for instance by a photoluminescent converter, it can be entirely separated from the injected and transmitted interrogating lights and measured directly. The measured intensity of the converted light will be proportional to the value of $\alpha$, not $(1-\alpha)$, and a change of one percent in the value of $\alpha$ will change the intensity of the measured luminescence light by 1.0 percent, not 0.01 percent like the change in the value of $(1-\alpha)$. The temperature measurement is then much more accurate and can be carried out with relatively inexpensive instruments, because the accuracy of the light intensity measurements needed to measure the temperature to within 1° C. is now one part per hundred (one percent) instead of one part per 10,000 (0.01 percent).

There is another important advantage: if one measures both the luminescence intensity emitted by the probe and the interrogating light transmitted by the probe, the ratio of these quantities can be used as an accurate temperature indicator. The ratio is unaffected or only minimally affected by fluctuations of the intensity of the interrogating light or by fiber and/or connector losses. The measurement requires a single interrogating light source, and if the luminescence has a relatively long decay time, like $10^{-4}$ seconds or longer, one can measure both the transmitted interrogating light and the luminescence light with a single photodetector, because the lights can be separated in the time domain. Using conventional light transmission measurements according to the Snitzer patent, a radiometric measurement requires at least two light sources and two photodetectors (see FIG. 6 of the Snitzer patent). And the accuracy of the system is still affected by fluctuations of the intensity of the light sources, because the fluctuations in one light source are not compensated by fluctuations in the other.

Other preferred embodiments of these probes include photoluminescent materials characterized by a luminescence quantum efficiency which remains essentially invariant or varies only minimally over a temperature range of operation of the probe, but have at least one other photoluminescence property which is a sensitive function of temperature over the same range, like a luminescence decay time $\tau$ which decreases substantially with increasing temperature. Such combination of properties permits the construction of sensor systems in which a single optical probe can be used for the following measurements:

a) simultaneous measurement of temperature and another physical parameter, using in a preferred embodiment a single light source and a single photodetector; or b) simultaneous measurement of two physically independent temperature indicators, using in a preferred embodiment a single light source and a single photodetector to provide self-checking operation of the sensor system.

Preferred probe materials having a temperature-dependent luminescence decay time have a luminescence efficiency which remains high even at temperatures high enough to generate the so-called "temperature radiation", also known as "black body radiation". This is radiation emitted without the need of optical excitation of the material, and is emitted by all materials, whether or not photoluminescent. While the intensity of the temperature radiation emitted by most materials is somewhat lower than that of an ideal "black body", it is strongly temperature-dependent in accordance with the well-known (since 1901) Planck's radiation law, which ushered in quantum physics. At temperatures of about 800 kelvins (527° C.) and higher it is known to be already intense enough to be easily measurable by the same photodetectors (most commonly silicon photodetectors) used for measuring.

The invention teaches how such systems can be constructed and how they can be operated, beginning with an explanation of how one can measure temperature with photoluminescent probes having a luminescence quantum efficiency which remains essentially invariant over at least a relatively large part of their usable temperature range.

DEFINITIONS

Within the context of this application, I am using the following definitions:

Light: optical radiation, whether or not visible to the human eye.

Occupancy number of an energy level: the fraction of the total number of molecules of a probe material occupying said energy level.

Vibronic material: any luminescent material whose molecular electronic ground energy level comprises a plurality of vibrational sublevels with energies higher that of the lowest occupied level of the material, said vibrational sublevels being so distributed as to cover an essentially continuous wide band of energies.

Vibronic level: a vibrational sublevel of the electronic ground level of a vibronic material, having an occupancy number which increases with increasing temperature.

Luminescence: Light emitted by a material upon absorption of light or other radiation of sufficient quantum energy. The term includes both fluorescence and phosphorescence.

Photoluminescence: Luminescence generated by the absorption of light.

Luminescence centers: atoms or molecules (including ions) of a photoluminescent material which absorb excitation light and emit luminescence light.

Luminescence quantum efficiency (also referred to as luminescence efficiency): the ratio of the number of luminescence photons emitted by a photoluminescent material to the number of photons of the excitation light absorbed by the material.

Luminescence decay time, $\tau$: the time after the cessation of the excitation radiation in which the intensity of the luminescence decays from $I_0$ to $I_0/e$, where e is equal to 2.71828 and $I_0$ is the luminescence intensity at any reference time chosen as "zero" time.

Luminescence time rate of decay: the inverse of luminescence decay time.

Physical Variable: any physical property whose magnitude can change. Examples: temperature, pressure, flow rate, position, liquid level, and the like.

Physical parameter: physical variable.

Interrogating light: illuminating light injected into an optical probe for the physical variable.

Excitation light: illuminating light which can generate luminescence in a photoluminescent material.

Light beam: light being propagated through an optical system, including optical fibers, regardless of degree of divergence.

DETAILED DESCRIPTION OF THE INVENTION

Figure 5:
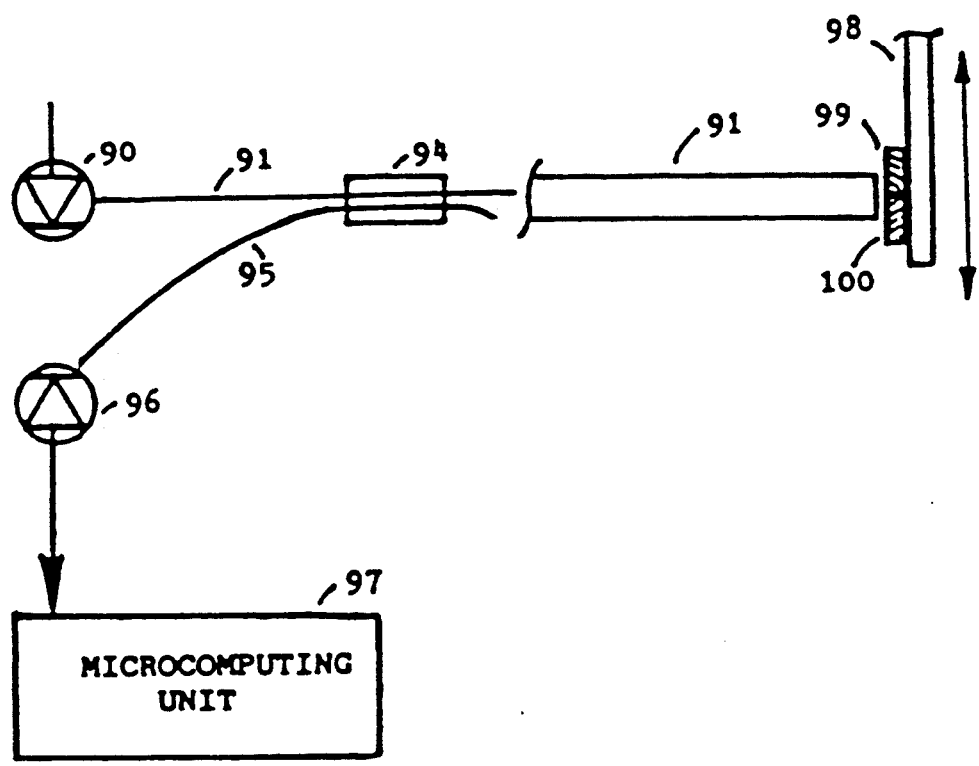
FIG. 5 illustrates an arrangement for the simultaneous measurement of temperature and position or displacement with a single probe.

1.0 Temperature Sensing Based on the Direct Measurement of Thermally Activated Light Emission Processes The techniques described in this section make use of thermally activated light emission from optical probes at wavelengths different from the wavelength or wavelengths of an interrogating light. A preferred embodiment uses photoluminescent probes, but does not require any photoluminescence property which varies with temperature over the temperature range being measured and can be implemented with probes made of virtually any solid or liquid photoluminescent material. These techniques were disclosed extensively in the preceding application Ser. No. 608,932 filed May 14, 1984, now U.S. Pat. No. 4,708,494. A thorough discussion is found in the specification of said patent, from column 6, line 50 to column 11, line 50. Device embodiments are described in column 15, lines 11-61 and FIGS. 1 and 5. A preferred embodiment uses probes operated according to the principles described and illustrated herein with reference to FIG. 1. The following analysis is deliberately oversimplified to emphasize the aspects most relevant to the invention. The quantitative relationships may not be followed rigorously in all practical systems.

Figure 1:
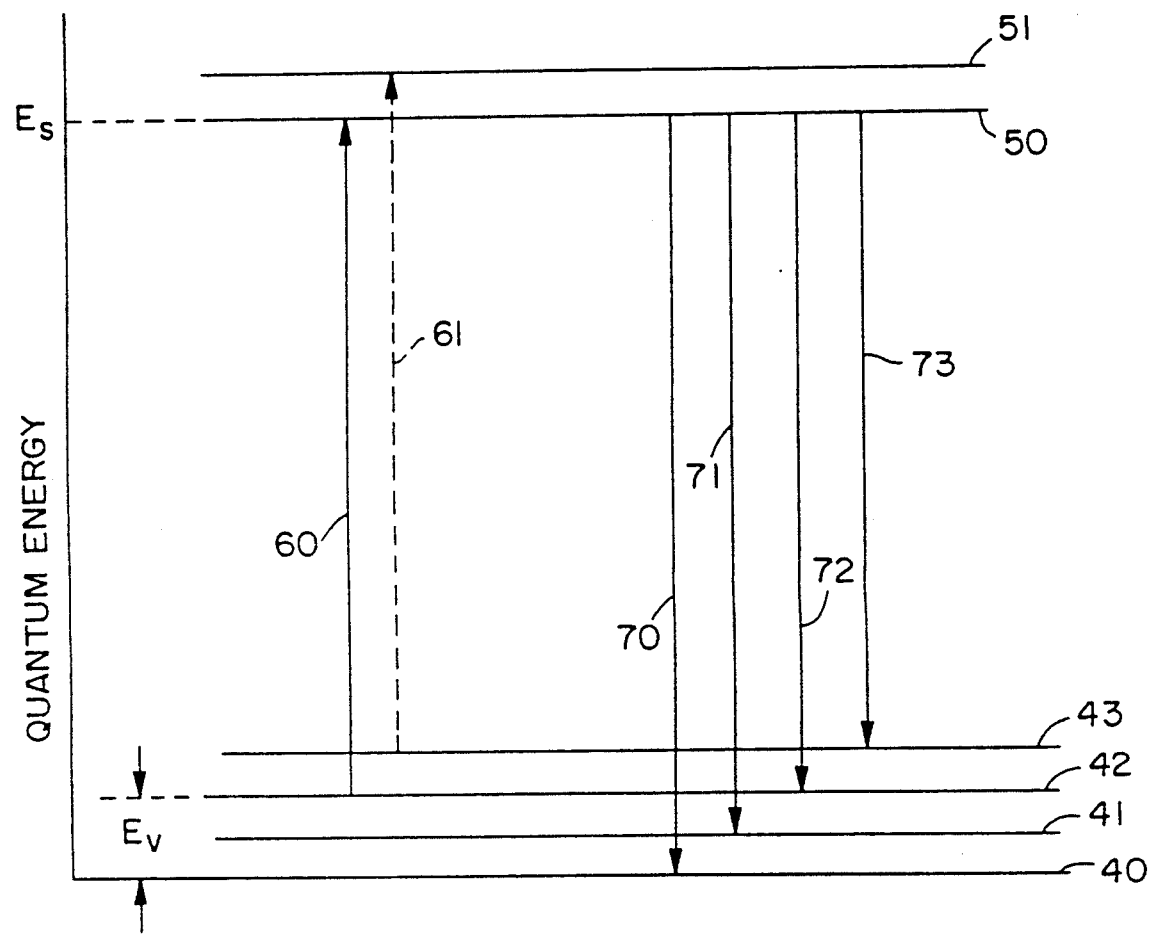
FIG. 1 is a simplified molecular energy diagram illustrating a temperature-dependent optical absorption process and luminescence conversion of the absorbed light in most photoluminescent materials.

FIG. 1 shows an electronic energy level diagram which at least qualitatively describes, at the molecular level, most photoluminescent materials. The photoluminescent material includes, at the atomic or molecular level, luminescence centers having a ground electronic level comprising vibrational sublevels 40, 41, 42, 43 and other sublevels which, for the sake of simplicity, are not shown. These materials are referred herein as "vibronic" materials. The lowest excited electronic energy comprises vibrational sublevels 50, 51, and other vibrational sublevels not shown. The vertical arrowed line 60 represents an optical electronic transition produced by the absorbed excitation light from level 42 to vibrational sublevel 50, which have fixed energy levels $E_v$ and $E_s$, respectively, relative to level 40. The length of line 60 corresponds to the photon energy of the optical transition and, hence, to the specific wavelength $\lambda_v$ of the excitation light. This wavelength obeys the relation $\lambda_v = hc/(E_s - E_v)$, where h Planck's constant and c is the velocity of light in a vacuum. The wavelength $\lambda_v$ can excite only molecules occupying vibronic level 42 and, to a smaller extent, molecules occupying slightly higher levels, the excitation of which is represented by the dotted vertical line 61. Luminescence emission occurs from sublevel 50 to the vibronic levels of the ground electronic level, said emission represented by lines 70, 71, 72 and 73. As shown in FIG. 1, a considerable spectral portion of the emission occurs at photon energies higher (and wavelengths shorter) than that of the excitation light, and is commonly referred to as anti-stokes emission.

In practice the vibronic material is often used as a solid solution, glassy or crystalline, which constitutes the temperature probe. The concentration of the vibronic material and the dimension of the probe along the direction of the interrogating light are chosen so that the probe absorbs only a fraction $\alpha$ of the intensity of the nearly monochromatic excitation light within the temperature range of operation, and transmits the rest. The absorbed fraction obeys the relation $$\alpha = 1 - 10^{-\epsilon c_o d (N_{42}/N)} \quad (1)$$

where $\epsilon$ is the molar decadic absorption coefficient of the molecules occupying the vibronic level 42;

$c_o$ is the molar concentration of the vibronic material;

d is the probe length in the direction of the incident excitation light;

$N_{42}$ is the number of molecules of the vibronic material occupying vibronic level 42; and N is the total number of molecules of the vibronic material The ratio $N_{42}/N$ essentially follows the relation $$N_{42}/N = f^{-1} \cdot \exp(-E_v/kT) \quad (2)$$

where F is the so-called partition coefficient of the molecular system, k is the Boltzmann constant and T is the absolute temperature. The expression $c_o \cdot f^{-1} \exp(-E_v/kT)$ is essentially the effective molar concentration of the molecules of the vibronic material occupying the vibronic level 42, and the quantity $10^{-\epsilon c_o d (N_{42}/N)}$ is the fraction of the intensity of the interrogating light transmitted by the probe (assuming no other light losses) and equal to $(1-\alpha)$. The ratio $E_v/k$ can be designated by the single constant $\beta$, for a given wavelength $\lambda_v$.

At optical densities no greater than about 0.02 $\alpha$ is given approximately by $$\alpha \approx 2.3\epsilon c_\rho df^{-1} \exp(-E_v/kT) \quad (3)$$

An analogous expression to $f^{-1}\exp(-E_v/kT)$ is $[\exp(E_v/kT)-1]^{-1}$, generally known as the Bone-Einstein population factor. As the value of $(E_v/kT)$ increases, especially at values greater than 3.0, the Bose-Einstein population factor becomes closer in magnitude to the Boltzmann factor $\exp(-E_v/kT)$.

At optical densities greater than 0.02 the relationship between $\alpha$ and the Boltzmann factor $\exp(-E_v/kT)$ becomes less linear, but equations (1) and (2) still hold, and the method can be used at high, low or intermediate optical densities.

The luminescence intensity $I_f$ generated by the interrogating light absorbed by the probe obeys the relation $$I_f = P_o(\lambda_v/hc)\alpha \cdot \Phi \text{ photons.sec}^{-1} \quad (4)$$

where $P_o$ is the radiant power, in watts, of the incident interrogating light, and $\Phi$ is the luminescence quantum efficiency of the vibronic material.

Probes made from materials having high $\Phi$ values can produce large signal-to-noise ratios even with optical densities lower than 0.01, provided that the optical system has at least a moderately high collection efficiency for the probe luminescence. With fiber optic systems, a collection efficiency of the order of 1 percent is sufficiently high for most applications. Such efficiency is easily obtainable with state-of-the-art systems.

The sum of the light intensity absorbed and the light intensity transmitted by a clear medium is constant. Therefore, as the magnitude of the absorbed fraction $\alpha$ increases with increasing temperature according to equation (3), the intensity of the transmitted light must decrease accordingly. Since according to equation (4) the luminescence light intensity is proportional to $\alpha$, it follows that the ratio of the intensity of the luminescence light to that of the transmitted light increases with increasing temperatures and this ratio can be used as a temperature indicator. The ratio is unaffected or minimally affected by fluctuations of the intensity of the interrogating light or by fiber and/or connector losses.

The temperature coefficient of the luminescence intensity at low optical densities can be derived from equation (3), and follows approximately the relation $$(1/I_o)(dI_f/dT) = E_v/kT^2 = \beta/T^2 \quad (5)$$

where $I_o$ is the luminescence intensity at a chosen reference temperature. For example, a material with an energy $E_v$ of 1200 cm$^{-1}$ has a coefficient of about two percent per kelvin at an ambient temperature of 295 K.

Equations (3) and (5) has been derived from concepts well known in the fields of molecular spectroscopy and luminescence physics and illustrated in the oversimplified model of the energy levels of a representative photoluminescent material in FIG. 1. An equation similar to equation (5) can be derived also in the case of other systems wherein the interrogating light also excites molecules occupying a thermally populated level with an energy $E_v$ above the ground level, as in anti-Stokes Raman scattering (emission) illustrated in FIG. 1A, involving the emission of radiation of wavelengths shorter than the wavelength or wavelengths of the interrogating light. It is well known that the intensity of anti-Stokes Raman scattering increases with increasing temperature approximately as a function of the Boltzmann factor $\exp(-E_v/kT)$.

Equations (3) to (5) show that the method of the preceding paragraphs requires only a temperature-dependent change in the optical absorption coefficient of the photoluminescent probe material at wavelengths corresponding to photon energies lower than the energy $E_s$ of the excited emissive level. This property is shared by virtually all solid and liquid photoluminescent materials. The method does not require any temperature-dependent changes in the luminescence quantum efficiency, spectral distribution or decay time. Therefore, and in contrast to all other prior art methods, it can be implemented with most efficient photoluminescent materials.

Figure 2:
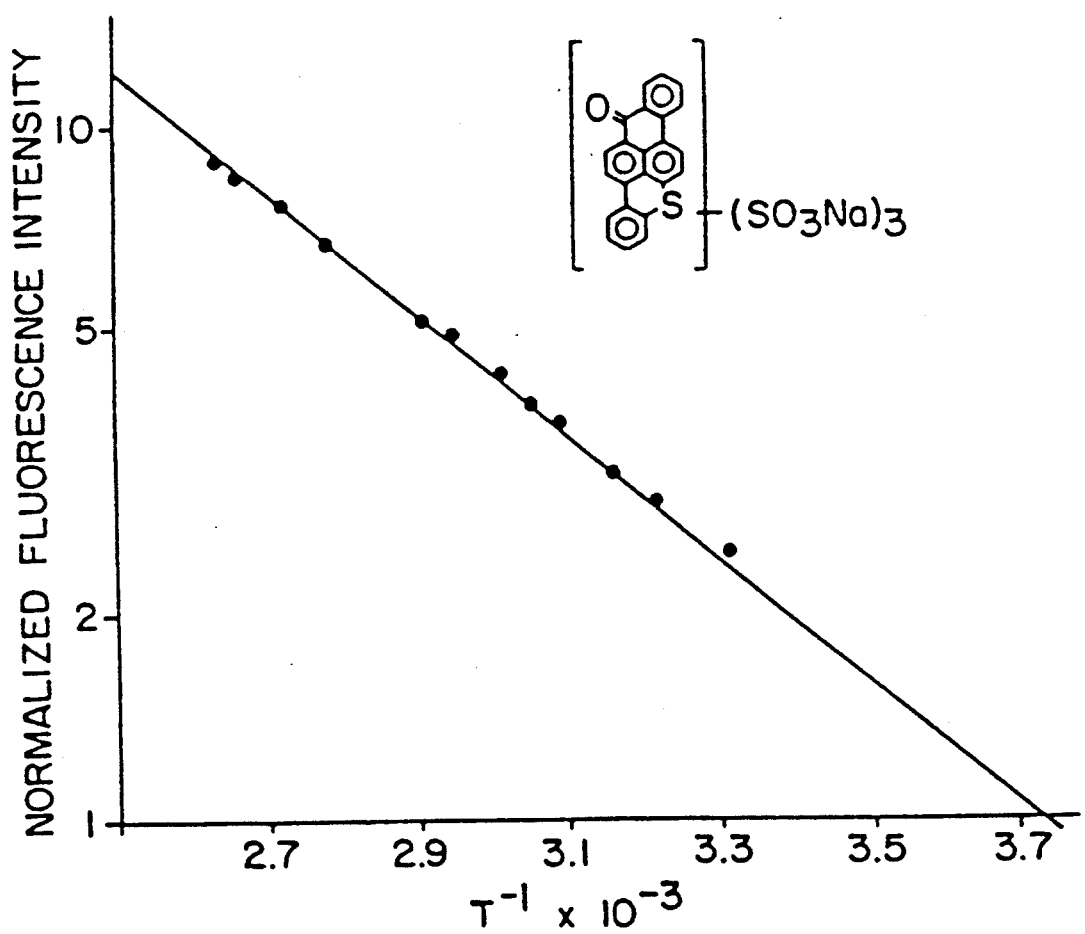
FIG. 2 shows the temperature dependence of the fluorescence intensity of a fluorescent material operated according to the principles illustrated in FIG. 1.

Experimental tests of equations (3) to (5) have been carried out during April and May of 1982, and the behavior predicted by the equations was verified. FIG. 2 shows actual normalized fluorescence intensity as a function of the inverse absolute temperature of a dimethyl sulfoxide (DMSO) solution of the dye represented by the formula

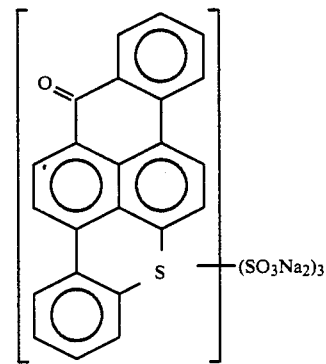

illuminated by a light beam from a helium-neon laser. The dye concentration was approximately $10^{-4}$ Molar, with a path length of 1 cm. The fluorescence intensity was monitored through a wavelength-selective optical filter which transmitted only light of wavelengths $\lambda_1$ of about 610 nanometers (nm), shorter than the laser beam wavelength of 632.8 nm. The superiority of this method of temperature measurement compared to that based on light transmission measurements becomes evident from the fact that over the temperature interval from about 300 K. (27° C.) to about 400 K. (127° C.) the light transmission of the dye solution varies by less than two percent, while the intensity ratio of fluorescence light to transmitted light varies by about an order of magnitude.

In the simplest embodiment of the method for temperature measurement according to this section, one only has to interrogate the photoluminescent probe material with light of a wavelength at which the probe material has a temperature-dependent absorption coefficient, and measure the intensity of the luminescence generated by the absorbed interrogating light. While the probe in the example of FIG. 2 is a liquid solution, solid probes, preferably in the form of optical fibers or inorganic crystalline materials, can also be used and are preferred in practical devices. As known to those of ordinary skill in the art, most inorganic photoluminescent materials wherein the luminescence centers are definite, stable atomic or molecular entities like transition metal ions and rare earth ions in a stable oxidation state, have luminescence properties which are unique and repeatable for each temperature within a temperature range typical for a specific material.

The above method can be implemented with any photoluminescent probe material having at least one energy level which can be thermally populated from the ground level to an extent that varies as a function of temperature. Such thermally populated level does not have to be a vibrational level or sublevel. It can be, for example, an electronic sublevel of the ground electronic level of a rare earth ion like $Nd^{3+}$. In this case, if the probe is interrogated with light of wavelengths of about 950 nm or other suitable wavelengths, the absorbed fraction $\alpha P_o$ of the interrogating light intensity, and hence the $Nd^{3+}$ luminescence intensity, increase with increasing temperature.

As stated in U.S. Pat. No. 4,708,494, col. 8, line 65 through col. 9, line 5:

... there are many luminescent vibronic materials having absorption and luminescence spectra over a wide spectral region from the ultraviolet to the near infrared. One can choose, therefore, the wavelength region most suitable to one's needs. For instance, if it is required to transmit the optical signal over long distances via an optical fiber, one could choose a material with absorption and luminescence bands at wavelengths longer than 700 nanometers (nm).

If the probe material is a glass or an optically homogeneous plastic, it can be made into an optical fiber.

An optical fiber temperature probe based on the measurement of a temperature-dependent light absorption measurement has an advantage over other optical probes in that it measures the average temperature over the length of the fiber probe. Thus, if one wishes to measure the average temperature over, for example, a pipe having different temperatures along its length, a long fiber temperature probe disposed over the whole length of the pipe will measure its average temperature. A preferred embodiment uses a luminescent probe with a temperature-dependent light absorption, the luminescence intensity of which follows approximately equation (4). Glass fibers doped with $Nd^{3+}$, $UO_2^{2+}$, $Mn^{2+}$ or any other luminescent ion are suitable. Also suitable, especially at temperatures not much higher than about 150° C. are plastic fibers doped with any plastic-soluble, stable fluorescent dye. Other preferred embodiments, suitable for operation over wider temperature ranges, use inorganic crystalline materials like Nd:YAG or the materials subject of section 2.0 discussed below. These materials include (among many others) emerald, a $Cr^{3+}$-doped beryl which can be used from the cryogenic regions up to over 500° C., as already pointed out in the parent application Ser. No. 608,932, now U.S. Pat. No. 4,708,494.

Figure 1A:
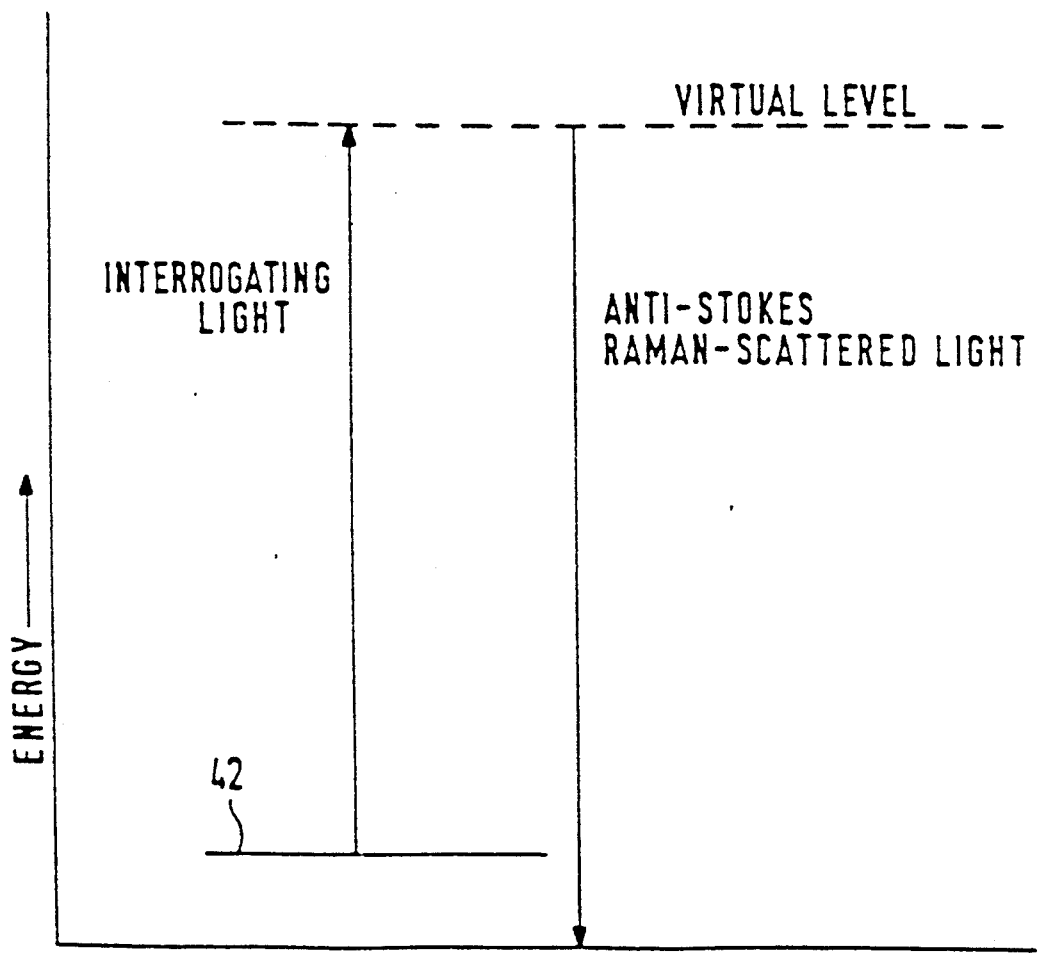
FIG. 1A is a simplified molecular energy diagram illustrating a temperature-dependent Raman scattering process in most materials.

A special case of the general phenomenon of anti-Stokes emission illustrated in FIG. 1 is anti-Stokes-Raman scattering, illustrated in FIG. 1A. Like anti-Stokes luminescence, anti-Stokes Raman scattering arises from the excitation of molecules occupying thermally populated energy levels, but the excitation is to a "virtual" level rather than to an actual level. Compared to anti-Stokes luminescence, anti-Stokes Raman scattering produces signals orders of magnitude weaker.

1.1 Fiber Optic Temperature Sensors Covering the Temperature Range from the Lower Cryogenic Regions up to Over 800° C. using a Single Probe.

FIG. I and equations (3) and (5) suggest how one may use a single probe for measuring temperatures over a very wide range from the lower cryogenic regions up to over 800° C., using a single probe with a high luminescence efficiency at these high temperatures, for example $Nd^{3+}$-doped yttrium aluminum garnet (Nd:YAG). One may choose the value of $E_v$ for each part of the range simply by choosing the wavelength $\lambda_v$ of the excitation source. Equation (5) suggests the $E_v$ values one may choose for any temperature range. Suppose than one requires a temperature coefficient of the signal of 0.01 or greater. At ordinary temperatures one may then use excitation wavelengths of about 950 nm from an inexpensive LED, corresponding to an $E_v$ value of about 750 $cm^{-1}$ and a signal temperature coefficient of about 0.012. For measuring cryogenic temperatures one can use a temperature-tunable diode laser emitting from about 807 nm to about 820 nm, spanning a range of selectable $E_v$ values from about 10 to about 200 $cm^{-1}$, usable from about 4.2 K. to about 60 K. For temperatures higher than 600 K. one may use a Nd-doped laser at 1.06 $\mu m$, corresponding to an $E_v$ value of about 1950 $cm^{-1}$.

The high luminescence efficiency of Nd:YAG at the above high temperatures was reported by Grattan et al., IEE Proceedings, Vol. 134, pp 291–294 (1987). Grattan et al. used the probe in the prior art conventional method based on the measurement of the temperature-dependent luminescence decay time $\tau$. The method has a very low sensitivity as the relative change in $\tau$ per kelvin is only of the order of $0.0001\tau$, in contrast to relative changes two orders of magnitude greater obtainable with the techniques of this invention as discussed in section 1.0. Used according to the teachings of this invention, temperature probes based on Nd:YAG and other probes having a high luminescence efficiency at high temperatures (for example an emerald probe operated at temperatures near 800 kelvins, as discussed in the parent application Ser. No. 608,932, now U.S. Pat. No. 4,708,494) have the additional and obvious advantage that, at the higher temperature range of their operation in the luminescence mode they inherently emit the so-called black body radiation of wavelengths within the range of operation of the same photodetectors used for measuring the photoluminescence of the probe. The intensity and wavelength distribution of the black body radiation is strongly temperature-dependent according to Planck's radiation law, well known since 1901. (Planck's radiation law is in fact the basis of temperature measurement with infrared radiometers). If one uses a probe comprised of, for example, Nd:YAG or emerald at the end of a heat-resistant fiber made of sapphire, the intensity of the black body radiation at the wavelength of, say, 1.0 $\mu m$, will be an accurate temperature indicator from about 800 K. (527° C.) to about 1,900° C. Since Nd:YAG emits its photoluminescence with a peak intensity at 1.06 $\mu m$ (near 1.0 $\mu m$, the same photodetector can be used to measure the black body radiation and the photoluminescence. Thus one can measure temperature anywhere from near absolute zero to well over 1500° C. with a single probe and a single photodetector. The above referenced paper by Grattan et al. actually discusses the black body radiation emitted by Nd:YAG at temperatures of 800 K. and higher, overlapping the photoluminescence from the same material.

Figure 3:
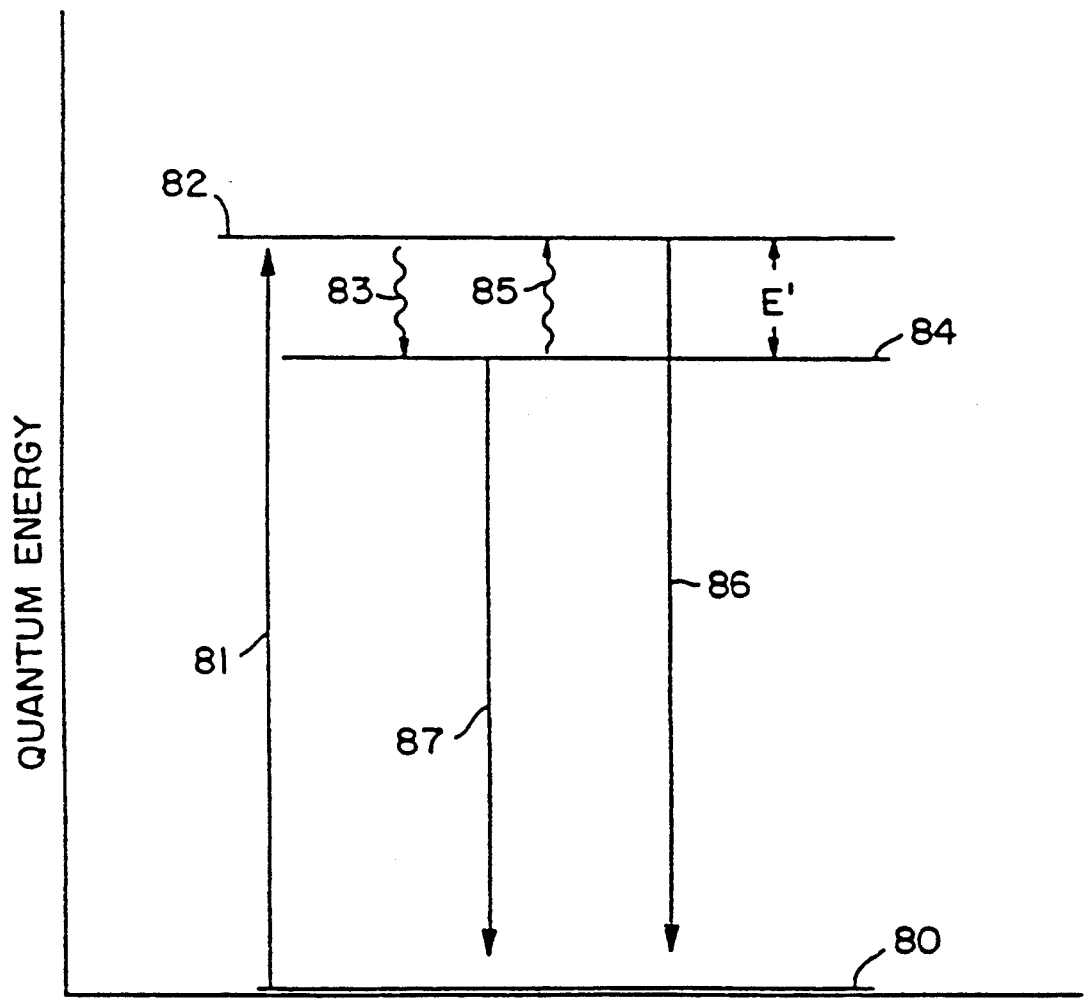
FIG. 3 is a schematic illustration of a temperature-dependent luminescence process determined by the thermal equilibrium between the occupancy numbers of two photoluminescent levels of a class of photoluminescent materials.

2.0 Luminescent Materials Having two Emissive Levels with Temperature-Dependent Relative Populations One preferred class of materials for the practice of this invention is actually a subclass of the materials which can be used according to the sensing techniques described in section 1.0 above. This subclass includes inorganic crystalline materials doped with luminescence centers so characterized that, when excited with light of a wavelength or wavelengths within an electronic absorption band characteristic of the material, they emit luminescence light from two excited levels the energies of which differ by the magnitude $E'$ and the relative occupancy numbers (populations) of which are a function of temperature within a range of temperatures. The temperature-dependent processes occurring in these materials are illustrated in FIG. 3, which is an oversimplified representative molecular energy diagram of the luminescence centers of such materials. As in section 1.0 above, the analysis that follows is deliberately oversimplified to emphasize the aspects most relevant to the invention. The quantitative relationships may not be followed rigorously in all practical systems. Molecules or ions of the luminescence centers occupying the ground level 80 are excited by absorption of light, as depicted by the arrowed line 81, to the emissive level 82, from which they decay rapidly, via the radiationless process 83, to the long lived excited emissive level 84. A fraction of the number of the molecules or ions occupying level 84 are thermally excited, via radiationless step 85, to emissive level 82, the occupancy number (population) of which, relative to level 84, follows approximately the relation (in absence of level degeneracy), $$(N_{82})/(N_{84}) = \exp(-E'/kT) \quad (6)$$

where $N_{82}$ and $N_{84}$ are the occupancy numbers (populations) of levels 82 and 84, respectively; k is the Boltzmann constant and $E'$ is the magnitude of the energy difference between these two levels. Equation (6) expresses what is generally known as the "Boltzmann population factor" of the molecules of a system occupying an energy level with an energy $E'$ relative to another, lower level. Levels 82 and 84 emit luminescence via radiative decays 86 and 87, with radiative rate constants $k_r'$ and $k_r$, respectively, with $K_r' >> K_r$. The ratio $R'$ of the luminescence intensity emitted from level 82 to that from level 84 follows approximately the relation (in the absence of level degeneracy)

$$R' = k_r'(N_{82})/k_r(N_{84}) \quad (7)$$

which can also be written as $$R' = (k_r'/k_r)\exp(-E'/kT) \quad (8)$$

Equation (8) shows that $R'$ increases exponentially with increasing temperature. The value of $R'$ can be measured by comparing the spectrally resolved luminescence intensities from each of the two emissive levels or, more conveniently, by measuring the decay time $\tau$ of the total luminescence of the material when excited with pulsed or AC-modulated interrogating light having a decay time much shorter than the luminescence decay time of the probe material. The luminescence decay time then decreases with increasing temperature according to the relation $$\tau = [1+\exp(-E'/kT)]/[k_r+k_r'\exp(-E'/kT)] \quad (9)$$

A measurement of $\tau$ (or its inverse, namely the time rate of luminescence decay) gives, therefore, an indication of the probe temperature. The preceding equations are applicable when the excitation light generates luminescence from only one kind of emissive centers in the probe. If this condition is not met the luminescence response may deviate somewhat from that predicted in the preceding equations. But such deviations do not affect the general validity and usefulness of this method of temperature measurement. In practice the probe is calibrated by recording a $\tau$ vs. temperature curve within the desired temperature range, with the aid of a precision reference thermometer, and storing said information in an electronic memory. Measurements made afterwards with the probe are compared automatically with the stored information by means of a microprocessor and/or other inexpensive electronic components, and the measured decay times are thus converted into reliable-temperature readings.

There are numerous probe materials which can be used with this method, and they include most efficient photoluminescent materials having a relatively fast-decaying emissive electronic energy level above and in thermal equilibrium with a relatively slow-decaying emissive level. Examples are numerous inorganic crystalline materials doped with $3d^3$ transition metal ions, which comprise the ions of trivalent chromium ($Cr^{3+}$), divalent vanadium($V^{2+}$) and tetravalent manganese ($Mn^{4+}$). Of these, the materials which behave according to the model of FIG. 3 include virtually all photoluminescent $Cr^{3+}$-doped or $V^{2+}$-doped materials wherein the $^4T_2$ level of the transition metal ion is higher than the $^2E$ level. $Cr^{3+}$-doped alkaline earth oxides, beryls and garnets are especially useful. Garnet crystals are widely used in electro-optic technology, especially the ubiquitous yttrium aluminum garnet (better known by its initials YAG), and other garnets often doped with $Cr^{3+}$ for use as wavelength-tunable lasers. Most photoluminescent $Cr^{3+}$-doped materials can be excited at wavelengths longer then 600 nanometers, compatible with inexpensive commercially available light-emitting diodes and laser diodes with light outputs in the red or near infrared regions, and their luminescence is emitted mostly at wavelengths longer than 700 nm, within the wavelength range of operation of inexpensive silicon photodetectors. The time rate of decay of their luminescence is unique and repeatable for each temperature over a wide temperature range, independent of the intensity of the excitation radiation or any prior illumination or temperature history.

One key advantage of these sensing materials, compared to prior art photoluminescent temperature probes based on a temperature-dependent luminescence decay time, is that the luminescence quantum efficiency does not decrease significantly over a temperature range over which the luminescence decay time varies substantially as a known, sensitive function of temperature. For example, the luminescence decay time of emerald (a $Cr^{3+}$-doped beryl), as reported in the above-cited reference by Fonger and Struck, Physical Review B, 11 pp 3251-3260 (1975), varies about 2 milliseconds at cryogenic temperatures to about 50 microseconds at about 130 degrees Celsius, a factor of about 40, with little or no change in luminescence quantum efficiency, unlike the prior art probes based on luminescence decay times, characterized by a large decrease in signal strength with increasing temperature. $Cr^{3+}$-doped YAG (Cr:YAG) behaves similarly, with a large temperature coefficient of its luminescence decay time over a wide temperature range in which the luminescence quantum efficiency remains high. The total luminescence quantum efficiency remains essentially constant or varies only minimally over a relatively wide temperature range over which the luminescence decay time undergoes relatively large measurable changes. This characteristic allows these materials to be used in probes for self-checking optical thermometry, and/or for the simultaneous measurement of temperature and at least another physical parameter with a single probe. The arrangements used for such measurements are described in sections 3.0 to 5.0, below.

Luminescence decay time measurements have an advantage over luminescence intensity measurements in that they do not require a simultaneous light transmission measurement for referencing. It is one of the teachings of this invention that one can use luminescence decay time measurements for measuring the temperature-dependent light absorption of some of the luminescent materials discussed in section 1.0 even if these materials do not have a temperature-dependent luminescence decay time. One way of doing so, described in the parent applications Ser. Nos. 405,732 filed Aug. 6, 1982, now abandoned and 608,932 filed May 14, 1984, now U.S. Pat. No. 4,708,494, is to incorporate in the material, in addition to the luminescence centers having a temperature-dependent light-absorption coefficient at the wavelengths of the excitation light (referred to herein as "A centers"), another kind of luminescence centers ("B centers[) which either do not have a temperature-dependent light absorption coefficient at said wavelengths, or have a light absorption coefficient which varies in a significantly different manner from that of the A centers. Now, if the A centers and the B centers have substantially different luminescence decay times, the measured luminescence decay time of the material including both kinds of centers will vary significantly as its temperature varies, because the relative numbers of luminescing A and B centers will vary. For example, an yttrium aluminum garnet (YAG) crystal co-doped with $Nd^{3+}$ and $Yb^3$ ions can be excited with light of wavelengths near 946 nm or any other wavelength at which the absorption by $Nd^{3+}$ is strongly temperature-dependent but the absorption by $Yb^{3+}$ is. only minimally affected by temperature. The luminescence from $Nd^{3+}$ peaks at about 1064 nm, and that from $Yb^{3+}$ peaks at about 975 nm. The relative intensities of both luminescences can be measured by using spectrally selective optical filters and measuring separately the luminescence intensities at 975 and 1064 nm. A simpler way, which does not require optical filters, is to pulse the interrogating light and measure the decay time of the total luminescence from both $Nd^{3+}$ and $Yb^{3+}$. The luminescence decay time of $Yb^{3+}$ is several times longer than that of $Nd^{3+}$. Thus, as the temperature increases, the luminescence intensity from $Nd^{3+}$ increases relative to that from $Yb^{3+}$, and the decay time of the total luminescence decreases as a function of said relative intensities.

It is not necessary for the luminescence centers to be in a crystalline matrix. The $Nd^{3+}$ and $Yb^{3+}$ ions may be dissolved in a glass matrix.

3.0 Self-checking Temperature Measuring Systems

If a single optical temperature probe could be operated in at least two independent modes, then a thermometer using that probe could be self-checking, that is, the temperature reading obtained from one mode of operation will agree with the temperature reading obtained from the other mode, if the device using the probe is functioning properly. The teachings of this invention permit self-checking operation of optical thermometers using a single luminescent probe. It has been pointed out already that the method for measuring temperature based on thermally activated light absorption and luminescence conversion of the absorbed light, as discussed in section 1.0 above, can be implemented with virtually any solid luminescent material. This method can be used with the luminescent materials subject of section 2.0, having a temperature-dependent luminescence decay time and a relatively high luminescence quantum efficiency over its temperature range of operation. It follows, then, that a temperature probe comprised of such material can be interrogated in two mutually independent modes, namely, a) a temperature-dependent optical absorption coefficient at a wavelength $\lambda_v$, and (b) a temperature-dependent luminescence decay time. When interrogated with pulsed or AC-modulated light of wavelength $\lambda_v$ and a sufficiently short decay time injected into the probe, the probe will give two mutually independent temperature indicators: a temperature-dependent time-averaged luminescence intensity $I_f$ proportional to the intensity of the interrogating light absorbed by the probe, and temperature-dependent luminescence decay time $\tau$, which is independent of the intensity of the absorbed interrogating light. If the temperature measuring device using the probe is functioning correctly, then the temperature readings obtained from the two temperature indicators should agree with each other. Failure to so agree will immediately reveal a malfunction of the device. A single photodetector may be used for measuring simultaneously, or nearly simultaneously, both $I_f$ and $\tau$.

4.0 The Simultaneous Measurement of Temperature and Another Physical Variable with a Single Probe A serious problem in the industrial measurement of physical variables other than temperature is that the signals from most transducers can be affected by temperature changes. One way to deal with this problem is to add a temperature probe to the device used for measuring the variable of interest, and apply a temperature correction factor to the readings. The luminescent materials described in section 2.0 above, having a temperature-dependent luminescence decay time at essentially constant luminescence quantum efficiency, make it possible to measure both temperature and another physical parameter, for example pressure or another force, with a single probe.

Figure 4:
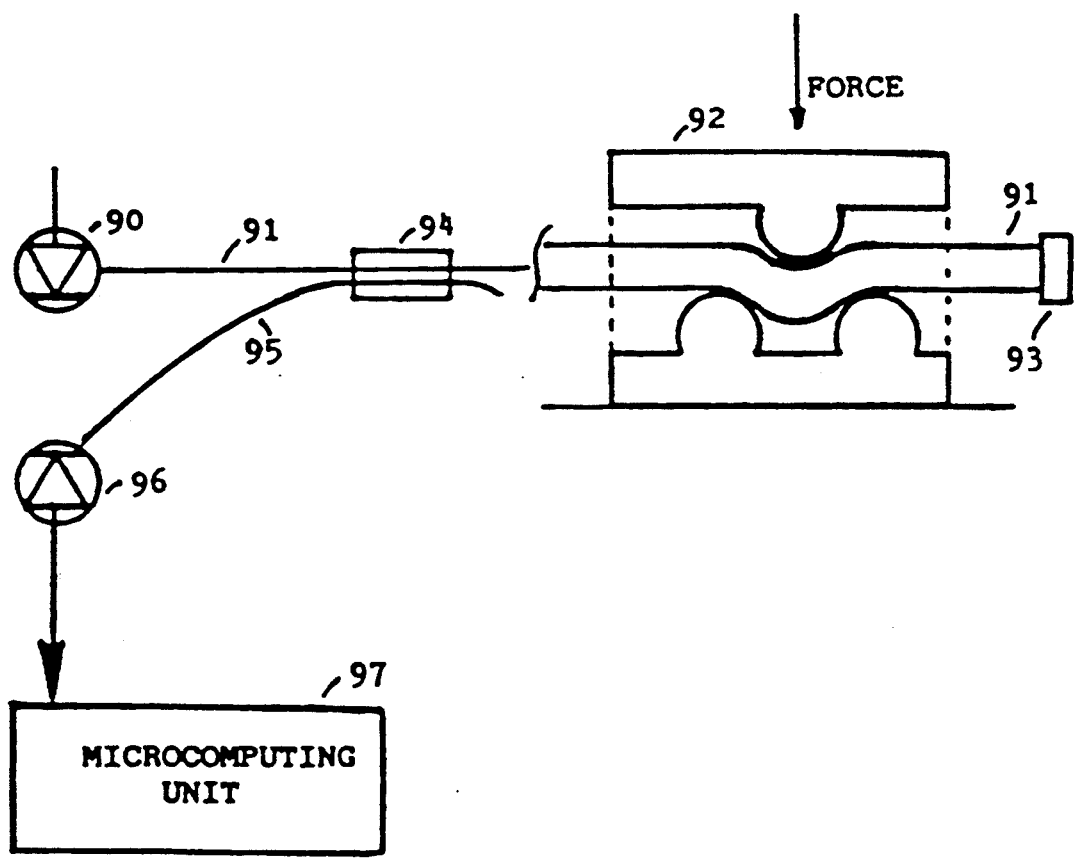
FIG. 4 illustrates an arrangement for the simultaneous measurement of temperature and pressure with a single probe.

One preferred embodiment of an arrangement for measuring both pressure and temperature with a single probe is shown in FIG. 4. A light source 90 injects interrogating light pulses of intensity $P_o$ and suitable wavelengths into an optical fiber 91 disposed within a fiber microbender 92 being acted upon by the force being measured. Attached to the distal end of the fiber is a luminescent tip 93 comprised of a material chosen from the class of materials described in section 2.0 above and FIG. 3, having an absorption band including the wavelengths of the injected light, a luminescence in response to the absorption of said light, the quantum efficiency of which is substantially invariant over a temperature range of operation of the device, and a luminescence decay time $\tau$ which is a sensitive function of temperature over the same range. Under the action of the force, the microbender 92 stresses the fiber 91 and causes an attenuation of the pulsed interrogating light of an intensity $P_o$ injected into the fiber to the attenuated intensity $P_o(1-\alpha)$, where the value of $\alpha$ is a function of the pressure applied to the microbender. The intensity of the light transmitted by the fiber under the microbender and incident on the luminescent tip 93 generates a luminescence therein with a time-averaged intensity $I_f$ which is an indicator of the pressure acting on the microbender, and is independent of temperature. On the other hand, the luminescence decay time $\tau$ of the probe is a temperature indicator, independent of the force applied to the microbender. A fraction of the intensity of the luminescence emitted by the tip 93 is collected by the same fiber 91 and directed, via fiber optic coupler 94 and the fiber segment 95, to photodetector 96. The force-dependent luminescence intensity If received by the photodetector and the luminescence decay time $\tau$ processed into both temperature and force readings at the microcomputing unit 97. One can thus measure both force and temperature with a single probe, a single light source and a single photodetector.

The duration of the interrogating light pulses should be preferable much shorter than the shortest decay time of the probe luminescence over the temperature range of operation of the device.

In an alternate embodiment one may use, instead of pulsed interrogation light, an AC-modulated interrogating light of a peak intensity which decays in a time shorter than the decay time of the probe luminescence,

5.0 The Measurement of Displacement and Temperature with a Single Probe

The luminescent materials discussed in section 2.0 above can be used as probes for the simultaneous measurement of displacement and temperature with a single probe, or for the simultaneous measurement of temperature and any parameter which controls the position or displacement of a probe. In one preferred arrangement, illustrated in FIG. 5, the probe is a screen 98 which moves along the directions of the arrows and includes two contiguous layers 99 and 100. Layer 99 is comprised of a $Cr_{3+}$-doped photo-luminescent material, for example Cr:YAG. Layer 100 is light-reflective. Opposite the screen is the distal tip. (tip opposite to the light injection tip) of the optical fiber 91 into which has been injected pulsed interrogating light beam of wavelengths within an optical absorption band of the $Cr_{3+}$-doped luminescent material of layer 99 and of a pulse duration much shorter than the luminescence decay time $\tau$ of this material. The electro-optical system is otherwise the same as that of FIG. 4. The distal tip of fiber 91 illuminates the screen 98 with an interrogating light spot, only part of the intensity of which is incident on the photoluminescent layer 99. As the screen moves, the relative intensities of the interrogating light incident on layers 99 and 100 vary as a function of the position of the screen, and the relative intensities of the light reflected from layer 100 and the time-averaged luminescence light emitted from the $Cr_{3+}$-doped layer 99 entering fiber 91 will be a function of said position. The luminescence decay time $\tau$ of layer 99 will be an accurate indicator of temperature, independent of the position or displacement of the screen.

In a simpler arrangement, one may omit the measurement of the intensity of the light reflected by the screen, as the intensity of the interrogating light incident on the luminescent probe, and hence the time-averaged intensity If of the probe luminescence, will vary with the position or displacement of the probe. The accuracy of the readings obtained with such arrangement may not be as high as those obtained by referencing said luminescence intensity to the intensity of the excitation light reflected by the probe, but should be sufficient for many industrial applications.

Any physical variable which can be converted into a displacement of an object can be sensed and/or measured with this technique. For example, if the screen 99 is attached to the push-rod of a pressure sensing diaphragm, then it could be used for the simultaneous measurement of both temperature and pressure.

In an alternate embodiment of the same invention, the luminescent screen is stationary and the distal tip of the optical fiber is attached to the object undergoing the displacement. The end result is the same: the intensity of the interrogating light spot incident on the luminescent material, and hence the intensity of the luminescence generated therein, varies as a function of the displacement of the object.

Since some changes may be made in the foregoing disclosure without departing from the invention herein disclosed, it is intended that all matter contained in the above description and depicted in the accompanying drawings be construed in an illustrative and not in a limiting sense.

I claim:

1. A fiber optic device for sensing temperature changes in an object or environment, including:
   (a) a probe comprised of photoluminescent material characterized by an ability to absorb a fraction $\alpha P_o$ of the intensity $P_o$ of interrogating radiation of suitable pre-selected wavelengths injected into the probe and emit luminescence radiation of wavelengths $\lambda_1$ different from the wavelength of the interrogating radiation and an intensity which varies as a known function of $\alpha$, where $\alpha$ is a fraction smaller than unity and increases with increasing temperature within at least part of the temperature range of operation of the device, said material including luminescence centers chosen from the group of $3d^3$ transition metal ions consisting of divalent vanadium, trivalent chromium and tetravalent manganese ions, the probe being further so characterized that, when excited with transient or periodic optical radiation of wavelengths within an absorption band of said material, it emits luminescence radiation with an intensity which decreases after termination of the excitation radiation with a decay time which decreases substantially with increasing temperature within a range of temperatures;
   (b) a source of said transient or periodic optical radiation;
   (c) fiber optic means for directing said transient or periodic optical radiation to said probe;
   (d) fiber optic means for directing a fraction of the intensity of the luminescence radiation emitted from said probe to photodetector means; and

21

(e) photodetector and associated electronic means for measuring the decay time of the luminescence emitted from said probe, said decay time being an indicator of the probe temperature.

2. A fiber optic device as claimed in claim 1 wherein the wavelengths of said transient or periodic optical radiation are longer than 600 nanometers and most of the intensity of said luminescence radiation is emitted at wavelengths longer than 700 nanometers.

3. A device as claimed in claim I wherein said luminescence centers are so characterized that, when excited with said transient optical radiation, they emit luminescence radiation with a total quantum efficiency which is substantially invariant or varies only minimally within a temperature range within which the luminescence decay time decreases substantially with increasing temperature.

4. A device as claimed in claim 3 wherein said luminescence radiation is emitted from two distinct excited electronic energy levels of said luminescence centers, one of said levels being higher than the other, the luminescence radiation emitted from said higher level having an intensity which increases with increasing temperature within a temperature range within which the quantum efficiency of the total luminescence is substantially invariant or varies only minimally.

5. A device as claimed in claim 3 wherein the wavelengths of said transient or periodic radiation are said preselected wavelengths at which the probe absorbs said temperature-dependent fraction $\alpha P_o$ of the intensity of said interrogating radiation, the device additionally including means for measuring the intensity of the luminescence radiation generated by the absorption of said fraction $\alpha P_o$ of the intensity of said interrogating radiation, said luminescence intensity being an additional indicator of the probe temperature.

6. A device as claimed in claim 3 and additionally adapted to sense a displacement or position of an object in addition to its temperature and using the same said probe, wherein said displacement varies the intensity of the interrogating light incident on said photoluminescent material in said probe, thereby varying the intensity of said luminescence light emitted by the probe and received by said photodetector means as a function of said displacement.

7. A device as claimed in claim 6 and additionally adapted to measure simultaneously both temperature and a force or pressure, wherein the position or displacement of said object is determined by the force or pressure applied on said object, and the magnitude of the force or pressure is indicated by the position or the magnitude of the displacement of said object.

8. A device as claimed in claim 2 wherein said decay time is within the range from $5 \times 10^{-5}$ seconds to $2 \times 10^{-3}$ seconds.

9. A device as claimed in claim 2 wherein the probe is additionally characterized by emitting said luminescence radiation at temperatures at which it also emits temperature radiation, also known as black body radiation, at wavelengths within the spectral range of operation of silicon photodetectors, the intensity of said black body radiation increasing as a known function of temperature.

10. An optical method for measuring the temperature of an object or environment, comprising the steps of:
(a) exposing a probe to the temperature to be measured, said probe including a photoluminescent material characterized by an ability to absorb a fraction $\alpha P_o$ of the intensity $P_o$ of interrogating radiation of suitable pre-selected wavelengths injected into the probe and emit luminescence radiation of wavelengths $\lambda_1$ different from the wavelength of the interrogating radiation and an intensity which varies as a known function of $\alpha$, where $\alpha$ is a fraction smaller than unity and increases with increasing temperature within at least part of the temperature range of operation of the device, said material including luminescence centers chosen from the group of $3d^3$ transition metal ions consisting of divalent vanadium, trivalent chromium and tetravalent manganese ions, the probe being further so characterized that, when excited with transient or periodic optical radiation of wavelengths within an absorption band of said material, it emits luminescence radiation with an intensity which decreases after termination of the excitation radiation with a decay time which decreases substantially with increasing temperature within a range of temperatures;
(b) illuminating said probe with said interrogating radiation generated by a suitable source, thereby generating luminescence radiation emitted by the probe;
(c) directing a fraction of the intensity of said luminescence radiation to photodetector means; and
(d) measuring the decay time of said luminescence radiation, said decay time being an indicator of the probe temperature.

11. A method as claimed in claim 10 wherein said interrogating radiation is directed from said source to the probe via fiber optic means, and said fraction of the intensity of said luminescence radiation is directed to photodetector means via fiber optic means.

12. A method as claimed in claim 10 wherein the wavelengths of said transient or periodic optical radiation are longer than 600 nanometers and at least a fraction of the intensity of said luminescence radiation is emitted at wavelengths longer than 700 nanometers.

13. A method as claimed in claim 10 wherein said luminescence centers are so characterized that, when excited with said transient optical radiation, they emit luminescence radiation with a total quantum efficiency which is substantially invariant or varies only minimally within a temperature range within which the luminescence decay time decreases substantially with increasing temperature.

14. A method as claimed in claim 13 wherein said luminescence radiation is emitted from two distinct excited electronic energy levels of said luminescence centers, one of said levels being higher than the other, the luminescence radiation emitted from said higher level having an intensity which increases with increasing temperature within a temperature range within which the quantum efficiency of the total luminescence is substantially invariant or varies only minimally.

15. A method as claimed in claim 13 wherein the wavelengths of said transient or periodic radiation are said preselected wavelengths at which the probe absorbs said temperature-dependent fraction $\alpha P_o$ of the intensity of said interrogating radiation, the method additionally including the step of measuring the intensity of the luminescence radiation generated by the absorption of said fraction $\alpha P_o$ of the intensity of said interrogating radiation, said luminescence intensity being an additional indicator of the probe temperature.

16. A method as claimed in claim 13 and adapted to sense the position or displacement of an object in addition to its temperature and using the same said probe, wherein said displacement is made to vary the intensity of the interrogating light incident on said photoluminescent material in said probe, thereby varying the intensity of said luminescence light emitted by the probe and received by said photodetector means as a function of said displacement.

17. A method as claimed in claim 16 and additionally adapted to sense simultaneously both temperature and a force or pressure using the same said probe, wherein force or pressure being sensed is made to change the position or displacement of said object as a known function of said force or pressure.

* * * * *